United States Patent [19]

Auner et al.

[11] Patent Number: 5,777,051
[45] Date of Patent: Jul. 7, 1998

US005777051A

[54] PHOTOLUMINESCENT SILACYCLOBUTENE MONOMERS AND POLYMERS

[75] Inventors: Norbert Auner, Berlin, Germany; Udo C. Pernisz, Midland, Mich.

[73] Assignee: Dow Corning Corporation, Midland, Mich.

[21] Appl. No.: 874,469

[22] Filed: Jun. 16, 1997

[51] Int. Cl.$^6$ .................... C08F 130/08; C08G 77/00; C07F 7/08

[52] U.S. Cl. .................... 526/279; 528/14; 528/32; 528/43; 528/25; 556/9

[58] Field of Search .................... 526/279; 528/14, 528/25, 32, 43; 556/9

[56] References Cited

PUBLICATIONS

Journal of Organometallic Chemistry, vol. 363, pp. 7–23, (1989).
Angew. Chem. Int. Ed. Engl., vol. 30, No. 9, pp. 1151–1152, (1991).
J. prakt. Chem., vol. 337, pp. 79–92, (1995).
Organometallics, vol. 12, pp. 4135–4140, (1993).
Bull. Soc. Chim. Fr., vol. 132, pp. 599–603, (1995).
Norbert Auner, Oskar Nuyken, Bettina Biebl Journal of Macromol., Sci., Pure Appl. Chem. A34(1), 225–234, Jan. 1997.

*Primary Examiner*—Joseph L. Schofer
*Assistant Examiner*—Wu C. Cheng
*Attorney, Agent, or Firm*—James L. DeCesare

[57] ABSTRACT

Silacyclobutene monomers, and polymers based on silacyclobutene building blocks, exhibit photoluminescence in the blue region of the visible spectrum when excited by ultraviolet light.

7 Claims, No Drawings

PHOTOLUMINESCENT SILACYCLOBUTENE MONOMERS AND POLYMERS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention is directed to new and novel silacyclobutene monomers and polymers.

While one co-inventor herein has authored and co-authored articles relative to silacyclobutenes, none of the articles describe monomers or polymers which replicate the monomers or polymers described herein. Reference may be had, for example, to *Angew. Chem. Int. Ed. Engl.*, Volume 30, No. 9, Pages 1151–1152, (1991); *Organometallics*, Volume 12, Pages 4135–4140, (1993); *Bull. Soc. Chim. Fr.*, Volume 132, Pages 599–603, (1995); and *J. Prakt. Chem.*, Volume 337, Pages 79–92, (1995).

BRIEF SUMMARY OF THE INVENTION

This invention relates to photoluminescent silacyclobutene monomers and polymers, and to methods of making such photoluminescent monomers and polymers.

The photoluminescent silacyclobutene polymers and monomers have structures which are represented by the following repeating units and formulas:

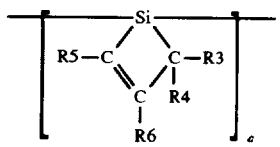

and

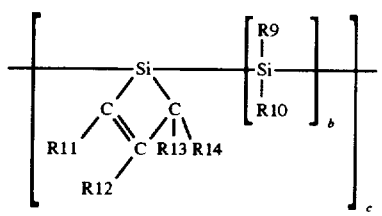

and

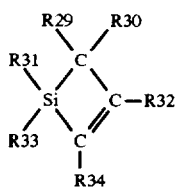

and

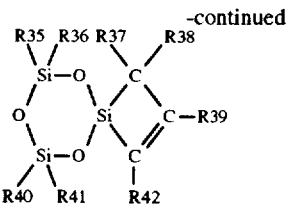

and

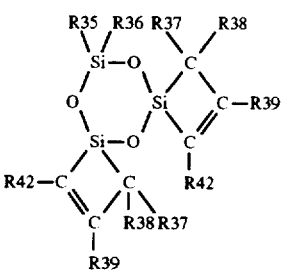

and

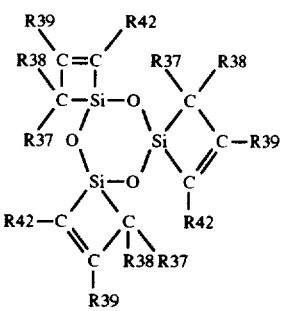

where the values of a, b, and c, and a definition of the R groups, are set forth below.

These and other features and objects of our invention will become apparent from a consideration of the detailed description.

BRIEF DESCRIPTION OF THE SEVERAL VIEWS OF THE DRAWING

Not applicable.

DETAILED DESCRIPTION OF THE INVENTION

This invention is directed to photoluminescent silacyclobutene monomers, and to photoluminescent silacyclobutene polymers having low to medium degrees of polymerization based on silacyclobutene building blocks.

Unexpectedly, it was found that these silacyclobutene monomers and silacyclobutene polymers exhibit strong photoluminescence in the blue region of the visible spectrum, when excited by ultraviolet (UV) light with a wavelength of 337 nanometer (nm).

One type of polymer representative of our invention is a polysilacyclobutene which has repeating units shown generically as:

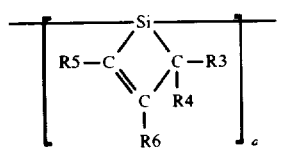

where a is an integer having a value of 3 to 20; R3 and R4 represent hydrogen or an alkyl group containing 2 to 10 carbon atoms; and R5 and R6 represent aryl groups. These polysilacyclobutenes are linear polymers which are terminated by suitable alkyl, alkoxy, aryl, or silyl groups.

One species (I) of the genus is shown below:

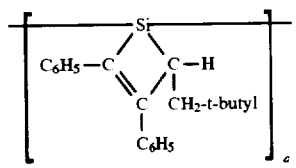

A compositional analysis of this polymer was carried out. Gel Permeation Chromatography revealed that the molecular weight of the polymer was 1,950 dalton (number average) with a dispersity of 1.64 (weight average 3,200 dalton). Thus, the average number a of repeat units for this polymer was seven. Ultraviolet Spectroscopy showed UV absorption maxima at 210 nanometer, 234 nanometer, and 284 nanometer.

Particles of the above polymer were irradiated with UV light at a wavelength of 337 nm generated by a pulsed nitrogen laser with 0.1 millijoule (mJ) per pulse. The photoluminescence was very bright whitish, barely blue, and well visible in ambient room illumination.

The process for making these types of polymers can be illustrated schematically as shown below:

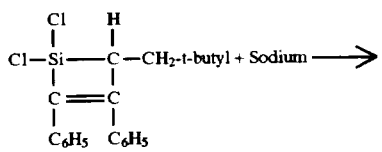

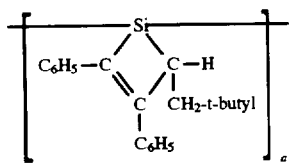

Other types of monomers can be used in this process such as monomers conforming to the formula

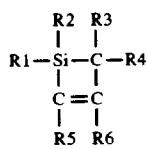

where R1 and R2 represent halogen or an alkoxy group; R3 and R4 represent hydrogen or an alkyl group containing 2 to 10 carbon atoms; and R5 and R6 represent aryl groups.

Isolation or recovery of these photoluminescent polysilacyclobutenes can be carried out by extraction, crystallization, or precipitation by addition of alcohol.

An example representing this process is set forth below in order to illustrate our invention in more detail.

EXAMPLE I

A silacyclobutene monomer of the structure represented below

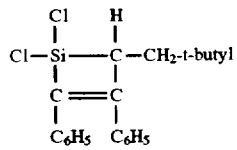

i.e., 1,1-dichloro-4-neopentyl-2,3-diphenyl-1-silacyclo-2-butene, was polymerized in toluene by refluxing it in the presence of sodium metal for ten hours. Ninety grams of polymer of the structure represented below

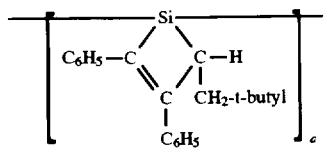

were recovered after removing the solvent. This polymer was identified as species (I) and a had an average value of seven.

Another type of silacyclobutene representative of our invention is a co-polymer which has repeating units which can be shown generically as:

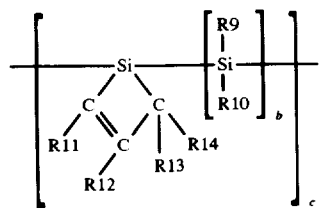

where b is an integer having a value of 1 to 15; c is an integer having a value of 2 to 20; R9 and R10 represent an alkyl group containing 1 to 10 carbon atoms or an aryl group; R11 and R12 represent an aryl group; and R13 and R14 represent hydrogen or an alkyl group containing 2 to 10 carbon atoms. These polysilacyclobutenes are linear co-polymers which are terminated by suitable alkyl, aryl, or silyl groups.

One species (II) of this genus is shown below:

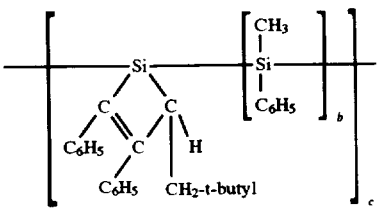

A compositional analysis of this co-polymer where b=9 was carried out. Gel Permeation Chromatography revealed that the molecular weight of the co-polymer was 3,620 dalton (number average) with a dispersity of 1.45 (weigh average 5,240 dalton). Thus, the average number c of repea units for this co-polymer was three.

Particles of the above co-polymer were irradiated with UV light at a wavelength of 337 nm generated by a pulse nitrogen laser with 0.1 millijoule (mJ) per pulse. The photoluminescence was very bright whitish, barely blue, and well visible in ambient room illumination.

The process for making this type of co-polymer can be illustrated schematically as shown below:

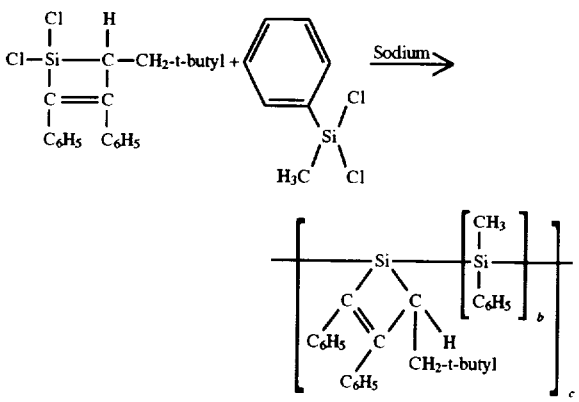

Isolation or recovery of these photoluminescent polysilacyclobutenes can be carried out by extraction, crystallization, or precipitation by addition of alcohol.

An example representing this process is set forth below in order to illustrate our invention in more detail.

EXAMPLE II

Example I was repeated, and a stoichiometric amount of phenylmethyldichlorosilane was added as another component of the polymerization mixture. Ten grams of co-polymer of the structure represented below

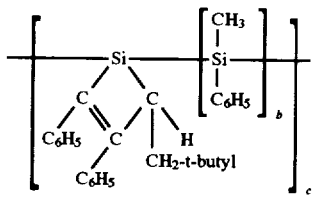

were recovered after removing the solvent. This co-polymer was identified as species (II) where b=9 and c=3. The process was carried out by drying the silacyclobutene monomer used in Example I, and storing it under nitrogen. The same procedure was carried out with the solvent. The silacyclobutene monomer and the phenylmethyldichlorosilane were transferred into a toluene solution containing about 0.7 to 1.3 mol/l toluene. Sodium metal was added in an exact stoichiometric quantity as granules. The reaction was carried out for 10 to 15 hours at 110° C. while refluxing the boiling toluene. The reaction solution was then reduced to half its volume and poured hot into methanol at 0° C. The product was isolated and dried. There was obtained a white to yellowish powder in a yield between 48% to 63% (species II).

By changing the amount of phenylmethyldichlorosilane relative to the amount of silacyclobutene monomer in Example I, different values of b can be obtained, before polymerization is initiated. This modification also causes changes in the molecular weight of the resulting co-polymer.

One silacyclobutene monomer representative of our invention can be shown generically as:

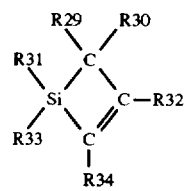

where R29 and R30 represent hydrogen or an alkyl group containing 2 to 10 carbon atoms; R31 and R33 represent hydroxyl, alkyl, aryl, alkenyl, or alkynyl groups; and R32 and R34 represent aryl groups. Some representative unsaturated groups are, for example, vinyl, allyl, H—C≡C—, $CH_3$—C≡C—, and aromatically substituted unsaturated groups such as $C_6H_5$—C≡C—.

One species (III) of this monomer genus is shown below:

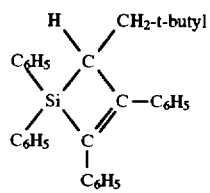

Particles of the above monomer III were irradiated with UV light at a wavelength of 337 nm generated by a pulsed nitrogen laser with 0.1 mJ per pulse. The photoluminescence was very bright, deep blue.

Isolation or recovery of this photoluminescent silacyclobutene monomer can be carried out by extraction, crystallization, or precipitation by addition of alcohol.

An example representing a process for making 1,1-diphenyl-4-neopentyl-2,3-diphenyl-1-silacyclobut-2-ene, i.e., monomer species III, is set forth below in order to illustrate our invention in more detail. In this example, photoluminescent silacyclobutene monomers are made by heating and stirring a reaction mixture containing a halosilacyclobutene, an organolithium reagent, and a solvent.

EXAMPLE III

To a solution of 10.0 grams (0.027 mol) 1,1-dichloro-4-neopentyl-2,3-diphenyl-1-silacyclobut-2-ene in 150 ml tetrahydrofuran (THF), was added a solution of 0.055 mol phenyllithium, freshly prepared from phenyl bromide and lithium in THF at −50° C. The reaction mixture was stirred and heated under reflux for three hours. The volatiles were removed under reduced pressure, and the residue was extracted twice with 75 ml pentane. After filtration, pentane was stripped off in vacuum, and an oily liquid product was transferred to a chromatographic column packed with silica gel. The product was eluted with ethyl ether. Further purification was conducted by high vacuum distillation, (boiling range 185°–190° C., $10^{-5}$ mbar), providing 8.4 grams (0.019 mol, 70%) of a white solid. The white solid (species III) was crystallized from a saturated $CH_3OH/C_2H_5OH/CHCl_3$ (10:2:1) solution at room temperature as white needles. Elemental Analysis for $C_{32}H_{32}Si$ ($M_r$, 444.70): Calculated: C, 86.43%; H, 7.25%; Si, 6.32%. Found: C, 87.53%; H, 7.36%.

While phenyllithium is shown in Example III as the organolithium reagent, other lithium alkyls or lithium aryls can be used, in order to make other different monomer species, such as methyllithium, tert-butyllithium, or hexyllithium.

A second species (III-A) of this monomer genus is a silanol functional monomer shown below:

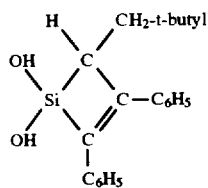

Particles of the above monomer III-A were irradiated with UV light at a wavelength of 337 nm generated by a pulsed nitrogen laser with 0.1 mJ per pulse. The photoluminescence was bright deep blue.

Isolation or recovery of this photoluminescent silacyclobutene monomer can be carried out by extraction, crystallization, or precipitation by addition of alcohol.

An example representing a process for making 2,3-diphenyl-4-neopentyl-1-silacyclo-2-butene-1,1-diol, i.e., monomer species III-A, is set forth below in order to illustrate our invention in more detail. In this example, photoluminescent silacyclobutene monomers are made by the hydrolysis of a halosilacyclobutene.

EXAMPLE III-A

A 250 milliliter three-necked flask equipped with a 100 ml dropping funnel and magnetic stirrer was charged with 100 ml of a saturated aqueous solution of sodium bicarbonate. Using an ice bath at 0° C., a solution of 10.0 grams of the silacyclobutene shown below (27.67 mmol) dissolved in 100 ml of diethylether, was added dropwise over a period of 20 minutes.

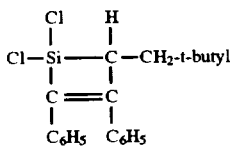

The mixture was stirred for 15 minutes, and 50 ml of diethylether was added to the cold mixture. Two layers separated, and the organic layer was washed twice by water, and the organic layer was dried over magnesium sulfate. The solvent was removed by evaporation, and a white, fine, light powder was obtained. The powder was purified by recrystallization from hot toluene. The resulting product was a fine, white, powder with a melting point of 171.14° C. Elemental Analysis for $C_{20}H_{24}O_2Si$ ($M_r$, 342.50): Calculated: C, 74.03%; H, 7.45%; O, 9.86%; Si, 8.66%. Found: C, 74.11%; H, 7.36%.

A third species (III-B) of this monomer genus is a phenylethynyl functional monomer shown below:

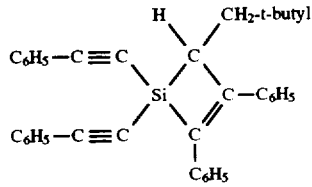

Particles of the above monomer III-B were irradiated with UV light at a wavelength of 337 nm generated by a pulsed nitrogen laser with 0.1 mJ per pulse. The photoluminescence was bright deep blue.

Other monomers representative of our invention are spiro-type cyclosiloxy-silacyclobutenes which can be shown generically as:

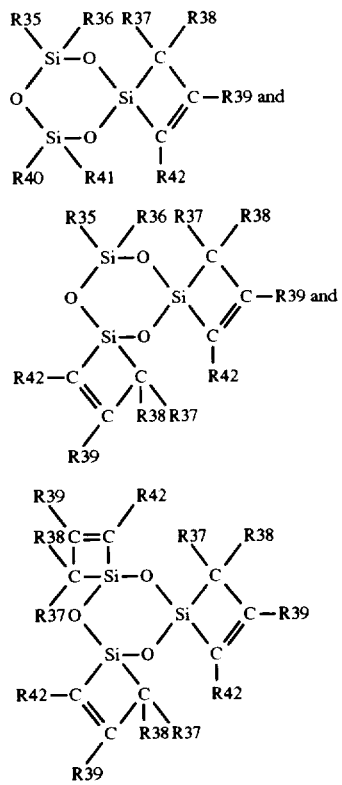

where R35, R36, R40, and R41 represent an alkyl group containing 1 to 10 carbon atoms or an aryl group; R37 and R38 represent hydrogen or an alkyl group containing 2 to 10 carbon atoms; and R39 and R42 represent an aryl group.

One species (IV) of monomer genus is shown below:

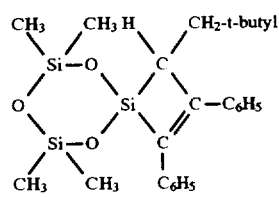

Particles of the above monomer were irradiated with UV light at a wavelength of 337 nm generated by a pulsed nitrogen laser with 0.1 mJ per pulse. The photoluminescence was very bright, deep blue.

Isolation or recovery of this photoluminescent spiro-type cyclosiloxy-silacyclobutene monomer can be carried out by extraction, crystallization, or precipitation by addition of alcohol.

An example representing a process for making monomer species IV is set forth below in order to illustrate our invention in more detail. The process involves the condensation of the silacyclobutene shown below

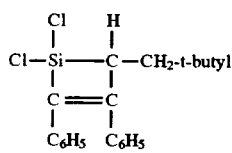

with 1,1,3,3-tetramethyldisiloxane-1,3-diol shown below

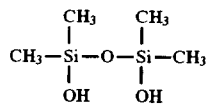

yielding monomer species IV, i.e., 1-(2',3'-diphenyl-4'-neopentyl-1-silacyclo-2'-butene)-3,3,5,5-tetramethylcyclotrisiloxane.

EXAMPLE IV

A 500 ml two-necked flask equipped with a 100 ml dropping funnel and magnetic stirrer was charged with a solution of 2 grams of 1,1,3,3-tetramethyldisiloxane-1,3-diol (12 mmole), and 2.6 ml of ethyldimethylamine in 200 ml of diethylether. To the flask was added dropwise at room temperature (20°–25° C./68°–77° F.), 4.35 grams of the silacyclobutene shown immediately above, dissolved in 100 ml of diethylether. The mixture was stirred for 30 minutes. The solution was washed several times with water, and the organic phase separated and was dried over sodium sulfate. The solvent was removed by evaporation, and a white powder was obtained. The white powder was purified by recrystallization in cold refrigerated pentane. The product was a white, hard, solid with a melting point of 136° C. Elemental Analysis for $C_{24}H_{34}O_3Si_3$ ($M_r$, 454.79): Calculated: C, 63.38%; H, 7.54%; O, 10.55%; Si, 18.53%. Found: C, 63.37%; H, 7.37%.

Another species (V) of monomer genus is shown below:

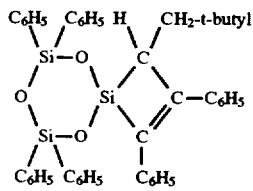

Particles of the above monomer were irradiated with UV light at a wavelength of 337 nm generated by a pulsed nitrogen laser with 0.1 mJ per pulse. The photoluminescence was very bright, deep blue.

Isolation or recovery of this photoluminescent spiro-type cyclosiloxy-silacyclobutene monomer can be carried out by extraction, crystallization, or precipitation by addition of alcohol.

Monomer species V is made in the same way as shown above in Example IV, except that the process involves the condensation of the silacyclobutene shown below

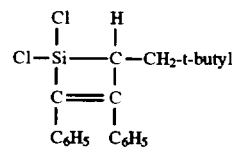

with 1,1,3,3-tetraphenyldisiloxane-1,3-diol shown below

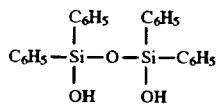

yielding monomer species V, i.e., 1-(2',3'-diphenyl-4'-neopentyl-1-silacyclo-2'-butene)-3,3,5,5-tetraphenylcyclotrisiloxane. Recrystallization of the product from warm pentane affords colorless crystals with a melting point of 156° C.

Although the photoluminescence of species (IV) and (V) was similar, the photoluminescence of species (IV) was about 1.5–2 times brighter than the photoluminescence of species (V).

The following example represents the process for making silacyclobutene monomer 1,1-dichloro-4-neopentyl-2,3-diphenyl-1-silacyclo-2-butene, i.e.,

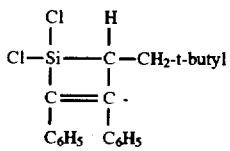

used in the above Examples.

EXAMPLE V

A 200 ml three-necked flask equipped with a 250 ml dropping funnel, magnetic stirrer, inert gas inlet, and pressure release valve, was charged with 50 grams (280.5 mmol) of diphenylacetylene, and 35.7 ml of trichlorovinylsilane (1 equ.) dissolved in 500 ml of pentane. Under an inert gas atmosphere, 167 ml of a 1.7 molar solution of tert-butyllithium in pentane (1 equ.), was added dropwise at room temperature until first fogging by precipitation of lithium chloride was observed. The remaining tert-butyllithium was added gently to prevent heating of the sample to the boiling point of the solvent. The mixture was stirred for ten hours to complete lithium chloride elimination. Precipitate was separated by filtration using a glass frit, and the solvent was removed by evaporation. The remaining yellow oil was fractionated by distillation to separate unreacted diphenylacetylene (boiling point 86° C./0.7×10$^{-6}$ mbar) from the product. Silacyclobutene monomer 1,1-dichloro-4-neopentyl-2,3-diphenyl-1-silacyclo-2-butene was yielded as 54.7 grams of a colorless, highly viscous oil (53.9% theor.) with a boiling point of 122° C./2×10$^{-6}$ mbar. Elemental Analysis for $C_{20}H_{22}Cl_2Si$ ($M_r$, 361.39): Calculated: C, 66.47%; H, 6.13%; Cl, 19.62%; Si, 7.78%. Found: C, 65.01%; H, 6.25%; Si, 7.72%.

Silacyclobutene monomers, and silacyclobutene polymers, according to our invention are useful as passive or active display materials, and also in electroluminescent devices. In such utility, they can be incorporated into road signs and lane markers. The monomers and polymers also find application in various types of displays as luminescent coatings for improving their visibility.

Other variations may be made in compounds, compositions, monomers, polymers, and methods described herein without departing from the essential features of our invention. The forms of invention are exemplary only and not intended as limitations on their scope as defined in the appended claims.

We claim:

1. Photoluminescent silacyclobutene monomers and silacyclobutene polymers having a repeating unit or formula selected from the group consisting of

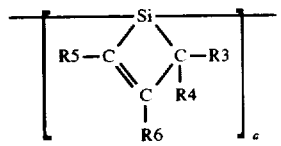

where a is an integer having a value of 3 to 20; R3 and R4 represent hydrogen or an alkyl group containing 2 to 10 carbon atoms; and R5 and R6 represent aryl groups;

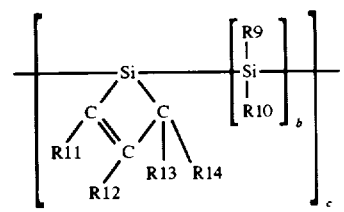

where b is an integer having a value of 1 to 15; c is an integer having a value of 2 to 20; R9 and R10 represent an alkyl group containing 1 to 10 carbon atoms or an aryl group; R11 and R12 represent an aryl group; and R13 and R14 represent hydrogen or an alkyl group containing 2 to 10 carbon atoms;

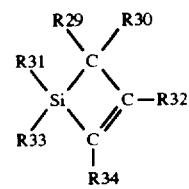

where R29 and R30 represent hydrogen or an alkyl group containing 2 to 10 carbon atoms; R31 and R33 represent hydroxyl, an alkyl, aryl, alkenyl, or alkynyl group; and R32 and R34 represent an aryl group;

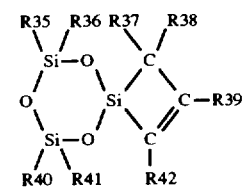

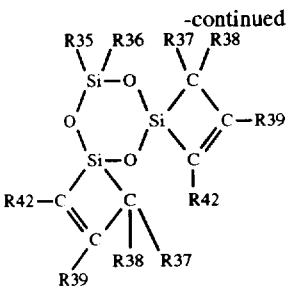

and

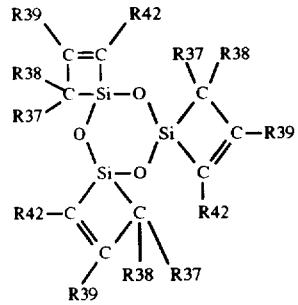

where R35, R36, R40, and R41 represent an alkyl group containing 1 to 10 carbon atoms or an aryl group; R37 and R38 represent hydrogen or an alkyl group containing 2 to 10 carbon atoms; and R39 and R42 represent an aryl group.

2. Photoluminescent silacyclobutene monomers and silacyclobutene polymers according to claim 1 exhibiting photoluminescence in the blue region of the visible spectrum when excited by ultraviolet light.

3. A method of making photoluminescent polysilacyclobutenes comprising polymerizing in a solvent containing sodium metal, a monomer having the formula

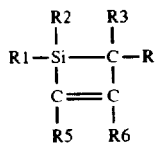

where R1 and R2 represent halogen or an alkoxy group; R3 and R4 represent hydrogen or an alkyl group containing 2 to 10 carbon atoms; and R5 and R6 represent aryl groups.

4. A method of making photoluminescent polysilacyclobutenes comprising polymerizing in a solvent containing sodium metal and an arylalkyldihalosilane, a monomer having the formula

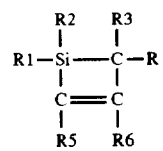

where R1 and R2 represent halogen or an alkoxy group; R3 and R4 represent hydrogen or an alkyl group containing 2 to 10 carbon atoms; and R5 and R6 represent aryl groups.

5. A method of making photoluminescent silacyclobutene monomers comprising heating and stirring a reaction mixture comprising a halosilacyclobutene, an organolithium reagent, and a solvent; the halosilacyclobutene being a monomer having the formula

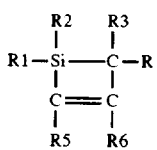

where R1 and R2 represent halogen or an alkoxy group; R3 and R4 represent hydrogen or an alkyl group containing 2 to 10 carbon atoms; and R5 and R6 represent aryl groups.

6. A method of making photoluminescent silacyclobutene monomers comprising hydrolyzing a halosilacyclobutene in the presence of a solvent at a temperature of 0°-25° C.; the halosilacyclobutene being a monomer having the formula

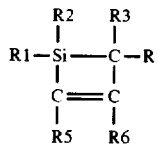

where R1 and R2 represent halogen or an alkoxy group; R3 and R4 represent hydrogen or an alkyl group containing 2 to 10 carbon atoms; and R5 and R6 represent aryl groups.

7. A method of making photoluminescent spiro-type cyclosiloxy-silacyclobutenes comprising condensing a halosilacyclobutene with a siloxane diol at room temperature; the halosilacyclobutene being a monomer having the formula

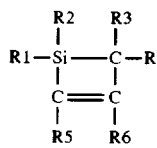

where R1 and R2 represent halogen or an alkoxy group; R3 and R4 represent hydrogen or an alkyl group containing 2 to 10 carbon atoms; and R5 and R6 represent aryl groups.

* * * * *